United States Patent [19]

Auer et al.

[11] 4,038,556
[45] July 26, 1977

[54] METHOD AND APPARATUS FOR SIMULTANEOUS OPTICAL MEASUREMENT OF PARTICLE CHARACTERISTICS

[75] Inventors: Robert Edward Auer, Miami, Fla.; Howard E. Tucker, Los Alamos, N. Mex.

[73] Assignee: Coulter Electronics, Inc., Hialeah, Fla.

[21] Appl. No.: 695,475

[22] Filed: June 14, 1976

[51] Int. Cl.² .............................................. G01N 21/26
[52] U.S. Cl. .................................... 250/575; 250/574; 250/539; 356/73; 356/152
[58] Field of Search ............... 250/573, 574, 575, 576, 250/461 B, 239; 356/73, 85, 201, 203, 39, 152

[56] References Cited

U.S. PATENT DOCUMENTS

| | | | |
|---|---|---|---|
| 3,535,539 | 10/1970 | Malespina et al. | 250/239 |
| 3,710,933 | 1/1973 | Fulwyler et al. | 356/39 X |
| 3,824,462 | 7/1974 | Mullaney et al. | 356/73 X |
| 3,918,812 | 11/1975 | Holm | 356/73 X |
| 3,938,895 | 2/1976 | Bridger et al. | 356/152 |

Primary Examiner—Rudolph V. Rolinec
Assistant Examiner—Vincent J. Sunderdick
Attorney, Agent, or Firm—Silverman & Cass, Ltd.

[57] ABSTRACT

A method and apparatus for simultaneous optical measurement of several characteristics of each particle of a group of small particles while the particles are suspended in a liquid. The apparatus includes a sample passage structure through which the particles pass, and a first optical detector structure which receives light from the sample passage structure. The sample passage structure and detector are aligned one with respect to the other. The output of a source of light is directed to the sample passage structure by an alignment device which aligns the light and the sample passage structure. A second optical detector receives the light passed by the sample passage structure. The second detector includes a converging lens and a photodetector so positioned with respect to one another that the light pattern at the detector due to the passage of a particle through the sample passage structure will maintain a substantially constant intensity notwithstanding movement of the sample passage structure, particle or the light.

54 Claims, 5 Drawing Figures

METHOD AND APPARATUS FOR SIMULTANEOUS OPTICAL MEASUREMENT OF PARTICLE CHARACTERISTICS

BACKGROUND OF THE INVENTION

The present invention relates to photo-analysis apparatus and more particularly to photo-responsive apparatus for detecting various characteristics of small particles.

There is a great need for accurate analysis of the characteristics of groups of small particles. A particularly important field for such analysis is in medical research and diagnosis. In this field, blood cells and other biological cells must be analyzed.

Many different types of apparatus have been employed to analyze small particles such as blood cells. When a number of characteristics of each cell are to be analyzed, optical analyzers are often employed. In this type of an apparatus, particles entrained in a very thin stream of liquid are passed one by one in the stream through an optical scanning station. Two or more photooptical detecting devices are arranged to detect the optical reaction of each particle to illumination from a beam of light cast through the optical scanning station. One detecting device measures the amount of fluorescence generated by passage of a particle through the beam of light, and a second detecting device measures the light scattered by passage of a particle through the beam of light.

In apparatus of this type, adjustment of the relative positions of the photo-optical detecting devices, the stream of liquid with particles therein,, and the light beam is extremely critical. Generally, one optical device, the fluorescence detector, is first aligned with the stream of liquid visually. The stream of liquid and the light beam are then aligned and the first photo-optical detecting device, the stream of liquid and the light beam all are again aligned with respect to one another in order to maximize the amount of light received by the detecting device.

The second photo-optical detecting device is then visually aligned with the liquid stream and with the light beam. Then its position is adjusted to maximize the light received at the photo-optical detecting device. Then all of the various structures are realigned with respect to one another by slight adjustments on each one in sequence until the alignment of all of the devices results in the maximum obtainable outputs.

It should be noted, however, that the maximum obtainable output of any one detector may not signify an optimized alignment, and an optimized alignment, because of the configuration of each structure, may not be possible. It should also be noted that the above described procedure for adjusting the apparatus is extremely difficult and time consuming, wasting time which could be more effectively utilized for actual testing procedures.

SUMMARY OF THE INVENTION

In practicing this invention, an apparatus is provided for simultaneous optical measurement of several characteristics of each particle of a group of small particles while the particles are suspended in a liquid. The apparatus includes a sample passage structure through which the particles pass and a first optical detector for receiving light from the sample passage structure and for developing first detection signals in response to the received light. Structure is provided in the apparatus for moving the sample passage structure and the first optical detector with respect to one another so that the two may be aligned with respect to one another. The apparatus also includes a source of light and a structure for directing light from the light source to the sample passage structure and for aligning the light and sample passage structure.

A second optical detector also is provided for receiving light from the sample passage structure and for developing a second detection signal in response to the received light. The second detector includes a converging lens for receiving the light from the sample passage structure and a photodetector positioned a predetermined distance from the focusing lens for receiving light from the focusing lens. The predetermined distance is selected such that the light pattern received by the photodetector due to the passage of a particle through the sample passage structure will maintain a substantially constant intensity with movement of any one of the sample passage structure, the particle therein, the light or the first detector. Consequently, the detector is insensitive to movement of any of the aforementioned structures and thus requires little or no alignment.

The method for aligning the apparatus structure so as to optimize results while utilizing a minimum number of alignment steps also is considered to be a part of this invention. Additionally, specific structures utilized as a part of the apparatus and alignment procedure also are considered to be novel.

DETAILED DESCRIPTION OF THE PREFERRED EMBODIMENT

Figure 1:
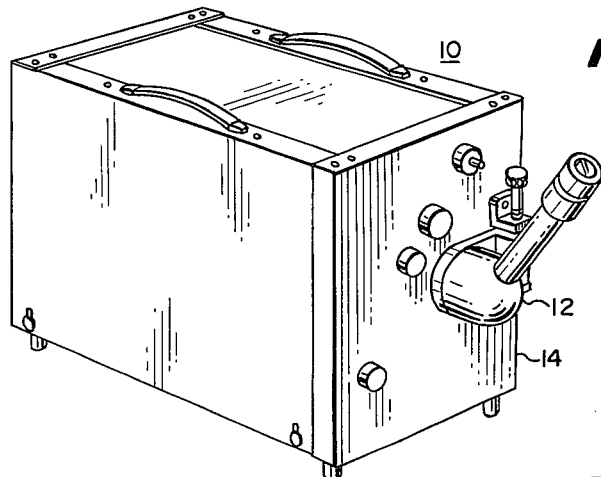
FIG. 1 is a perspective view of the entire apparatus with the cover in place and showing the observation microscope.

Referring to FIG. 1 there is shown a perspective view of the overall photoanalysis apparatus 10. A microscope 12 is secured to the front cover 14 of apparatus 10, the microscope allowing visual observation and alignment of the various portions of the apparatus shown in detail in FIG. 2.

Figure 2:
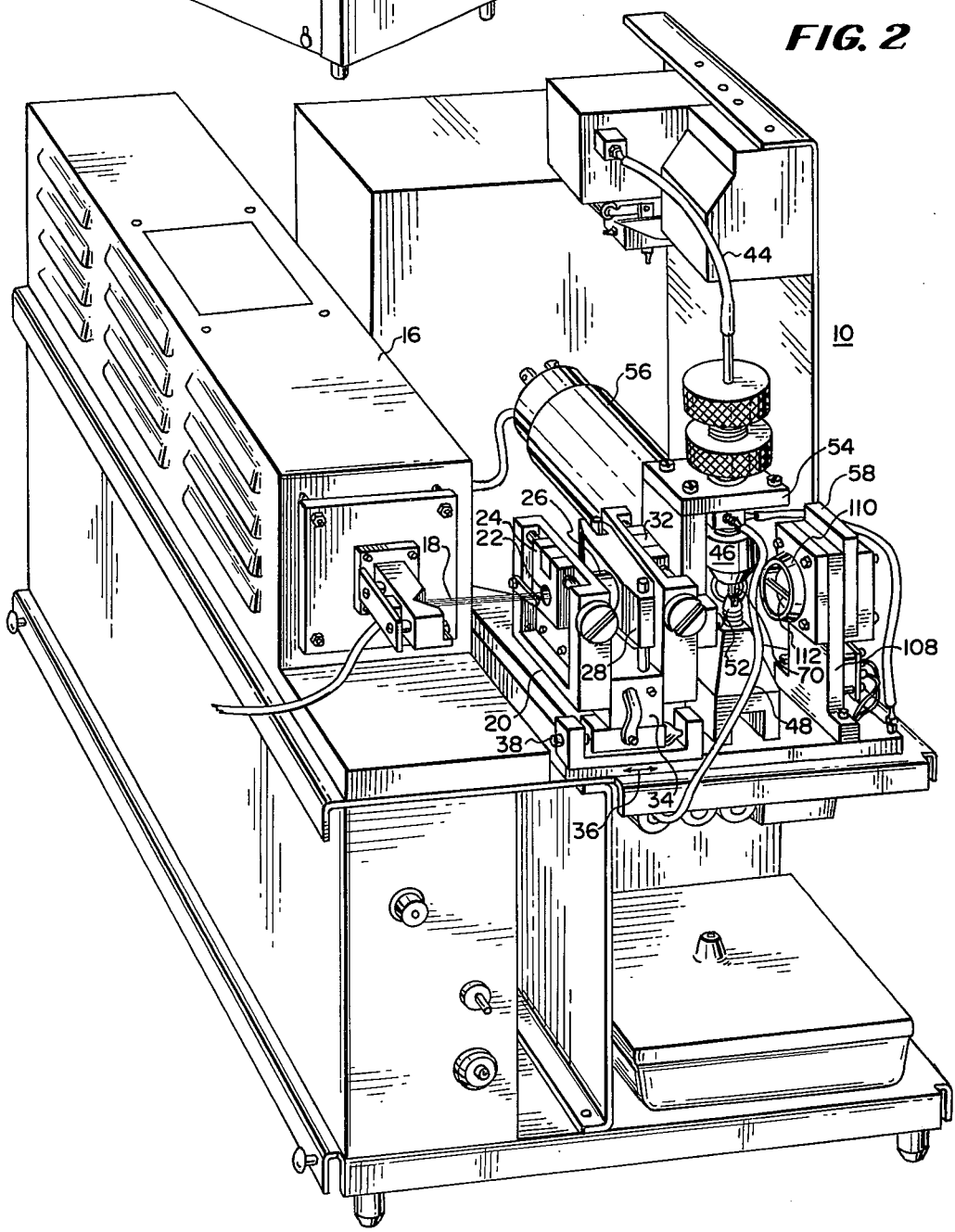
FIG. 2 is a partially exploded perspective view of the apparatus of this invention with the cover removed showing the various structures forming the apparatus.

Referring now to FIG. 2, a laser device 16 in photoanalysis apparatus 10 develops a laser beam 18, which, by a series of mirrors in laser 16 is emitted at right angles to the body of laser 16. Laser beam 18 is projected to and through an optical bench 20, which includes a first lens 22 mounted in a lens holder 24, a second lens 26 mounted in a second lens holder 28 and a mounting block carrier 32. Lens holders 24 and 28 and carrier 32 are carried by mounting block 34 which is movable in the direction indicated by arrow 36 in FIG. 3 by way of adjustment screw 38.

In apparatus 10, particles, such as blood cells, are entrained in a very thin stream of liquid and are passed one by one in the stream through beam 18 where the particles are detected. The stream is then broken into separate droplets and the detected particles are sorted. This portion of the apparatus is an outgrowth of the apparatus disclosed in U.S. Pat. No. 3,380,584 to M. J. Fulwyler and will not be discussed in detail.

Particles such as blood cells to be analyzed, in a highly dilute solution, are introduced into photoanalysis apparatus 10 through a conduit 44 to an ejection nozzle 46. A continuous flow of cell free liquid, known as sheath liquid, is introduced into ejection nozzle 46 by way of conduit 48 and flows coaxially around the cell stream. Ejection nozzle 46 also has a vibrational device therein such as is taught in the aforementioned Fulwyler patent for causing the stream to be separated into separate droplets. When leaving ejection nozzle 46, a cell stream 50 is formed which intersects laser beam 18 exiting optical bench 20 from carrier 32. The intersection occurs at a first location intersection 40. The cell stream then passes to a stream charging and deflecting apparatus 52 which separates droplets containing desired particles as is taught in the aforementioned Fulwyler patent.

Ejection nozzle 46 is mounted on a mounting block 54 which is secured to mounting block carrier 32. Mounting ejection nozzle 46 to mounting block carrier 32 allows movement of the nozzle 46 for alignment purposes as will be explained in greater detail subsequently.

When a particle entrained in cell stream 50 passes through laser beam 18, the laser beam itself may be scattered somewhat by the particle and the laser light may cause the particles to fluoresce and emit a fluorescent light. The fluorescent light developed by the particle is coupled to and detected by a first optical detector identified generally by the number 56; and the light scattered by passage of a cell through the laser beam 18 is coupled to and detected by a second optical detector identified generally by the number 58.

Figure 3:
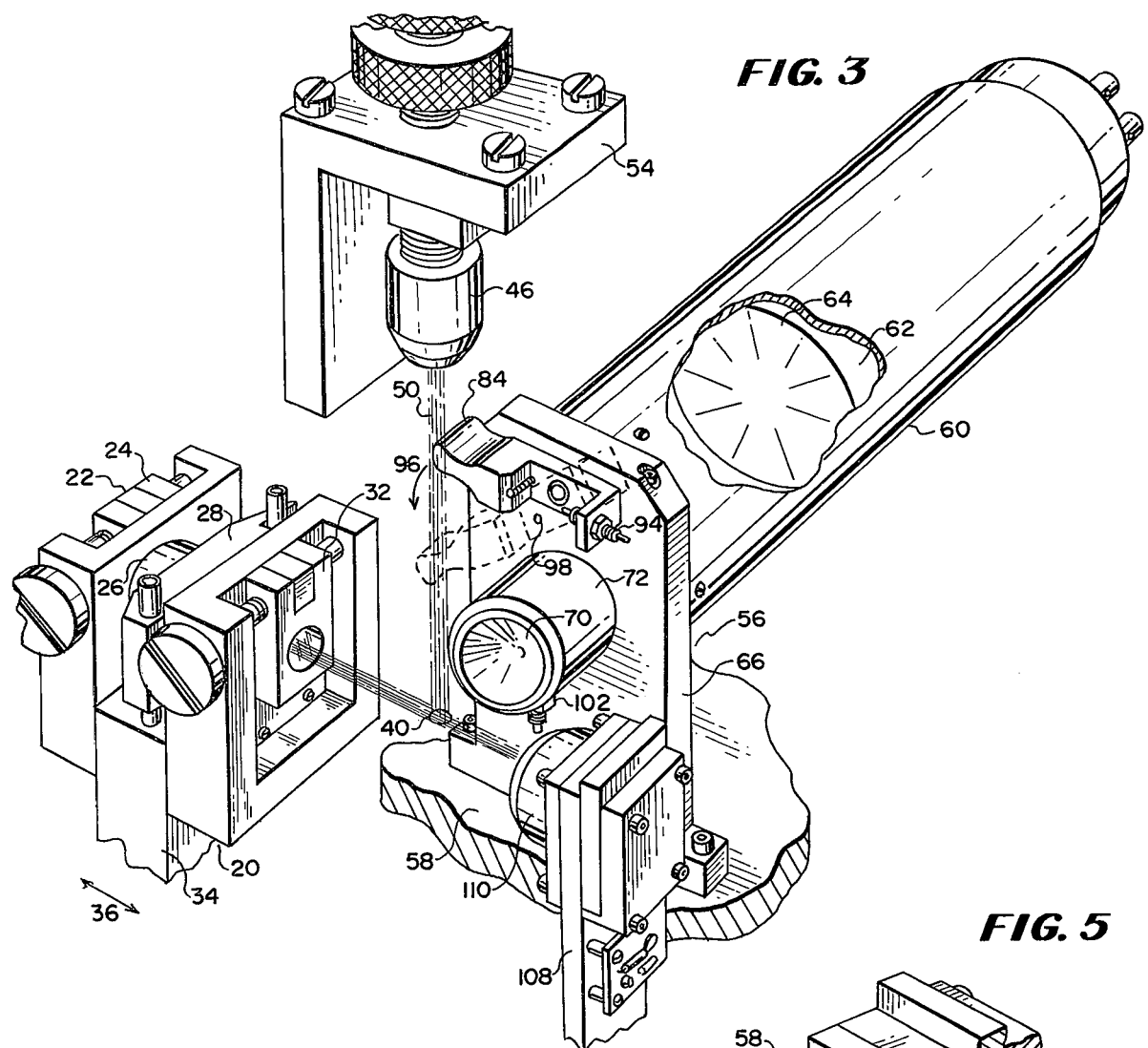
FIG. 3 is a perspective view of the structure which forms the apparatus shown in FIG. 2.
Figure 4:
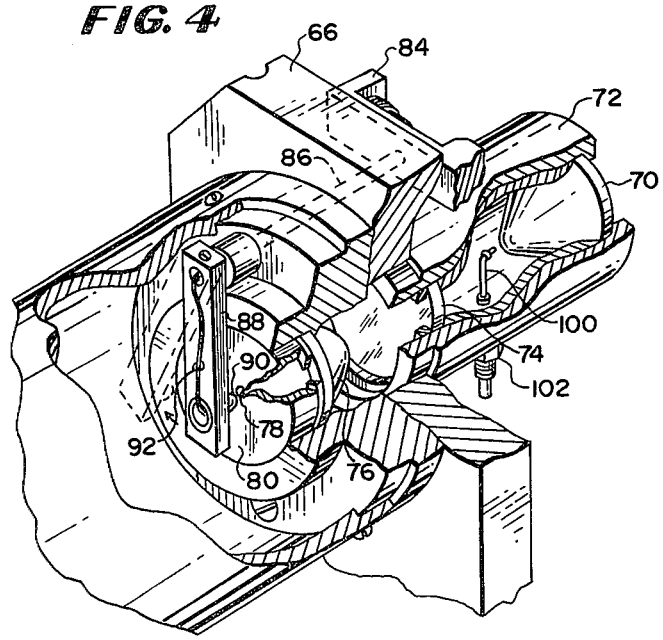
FIG. 4 is a partial cutaway view of the photomultiplier tube assembly shown in FIG. 3.
Figure 5:
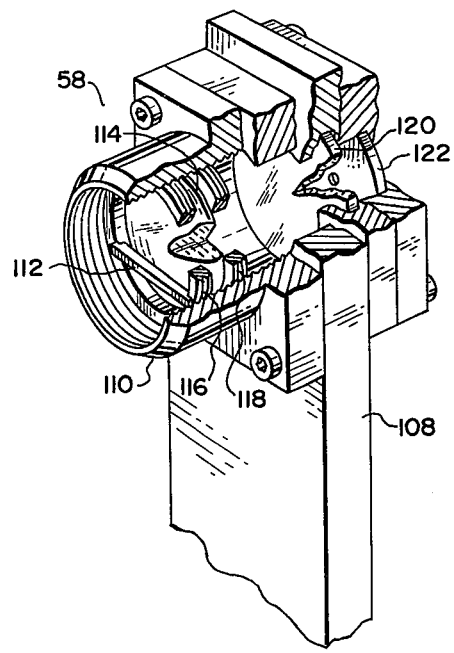
FIG. 5 is a cutaway view of the second photodetector assembly in the apparatus shown in FIGS. 2 and 3.

First optical detector 56 shown in greater detail in FIGS. 3 and 4, includes an elongate cylindrical housing 60 which encloses and supports a photomultipliter tube 62 which also is generally cylindrical in form and which has an end wall 64 forming a photosensitive screen. The housing 60 also has an end wall 66 which lies in a plane parallel to the plane of photosensitive screen 64 and through which an optical path is provided for coupling the fluorescent light developed at the first location 40 to the photomultiplier tube 62. The optical path is shown more clearly in FIG. 4 and includes a first aspherical lens 70 mounted in cylindrical holder 72.

First aspherical lens 70 receives the fluorescent light from first location intersection 40 and forms the light received into parallel beams which are projected back through cylindrical holder 72 to and through a filter 74 to a second aspherical lens 76 mounted into the end wall 66. The parallel light beams received by second aspherical lens 76 are focused at an aperture 78 in an aperture plate 80. The focused light passing through aperture 78 in aperture plate 80 is coupled to photomultiplier tube 62, where the light projected on the photosensitive screen 64 is converted into electrical signals which are analyzed to identify characteristics of the detected cell.

Two separate mechanisms, incorporated into first optical detector 56, are employed in aligning, adjusting and synchronizing the photoanalysis apparatus 10. The first mechanism includes a lever arm 84 which is secured to a first end of a hollow shaft 86, shown in dashed line representation in FIG. 4. Shaft 86 extends from a point outside of cylindrical housing 60, at which point is mounted lever arm 84, to a point inside of housing 60 and slightly beyond the location of aperture plate 80. Shaft 86 is loosely mounted in end wall 66 of housing 60 allowing rotation of shaft 86 therein. A light support bar 88 has one end secured to the end of shaft 86 positioned interior to housing 60 and adjacent aperture plate 80. The far end of light support bar 88 has mounted thereon a light structure 90, the particular light structure employed being a light emitting diode. A pair of conductors 92 are connected to light emitting diode 90 and extend through hollow shaft 86 to an electrical connector 94 mounted on lever arm 84. A power supply may be connected to connector 94 in order to supply electrical current to light emitting diode 90 for producing light output therefrom.

Lever arm 84 may be moved to either one of two positions by movement in the direction shown by arrow 96 in FIG. 3, one position being shown in FIG. 3 by the solid line representation of lever arm 84, and the second position being shown by the dotted line representation of lever arm 84. Lever arm 84 is held in either one of the two positions by means of detents formed in housing end wall 66 with one of the detents 98 being shown in FIG. 3. When lever arm 84 is in the position represented by the solid line drawing shown in FIG. 3, light support bar 88 is in a position directly behind aperture 78 in aperture plate 80 and light emitting diode 90 is positioned directly behind aperture 78. When lever arm 84 is moved to its second position represented by the dashed line location of lever arm 84 in FIG. 3, light support bar 88 is pivoted to its second, storage position, shown in dashed lines in FIG. 4. In this second, storage position, both light support bar 88 and light emitting diode 90 are moved away from aperture 78 so that any light passing through aperture 78 directed towards photomultiplier tube 62 passes freely and is not interfered with by the positioning of bar 88 and light emitting diode 90. Because of the close proximity of bar 88 and light emitting diode 90 to aperture 78, as long as these structures are out of the immediate field of aperture 78, they will not interfere with any light passing through the aperture to photomultiplier tube 62. Thus, when light support arm 88 is moved to its second position, light emitting diode 90 will be out of the immediate field of aperture 78 and there will be no interference.

Aperture plate 80 and aperture 78 are positioned one focal length of lens 76 behind lens 76 so that all parallel beams of light received by lens 76 are focused into aperture 78. As the light emitting diode 90 is positioned directly behind aperture 78, when diode 90 is energized, the light produced thereby will pass through aperture 78 to aspherical lens 76. Aspherical lens 76 directs the light received from diode 90 in parallel beams to aspherical lens 70 which focuses the beams received at a point in space in front of lens 70. The particular point in space at which the beams are focused is the front focal point of aspherical lens 70. From simple optics, any point source of light positioned at the front focal point of aspherical lens 70 will again focus to a point source of light at the back focal point of aspherical lens 72, which is the point at which aperture 78 in aperture plate 80 is located. When light emitting diode 90 is energized, a light image will appear in space in front of aspherical lens 70 and will be in focus at the front focal point of aspherical lens 70. This light image will be utilized in aligning photoanalysis apparatus 10 as explained in greater detail subsequently.

A second mechanism is also provided in first optical detector 56 and this consists of a light emitting diode 100 mounted in cylindrical holder 72 between first aspherical lens 70 and filter 74. Light emitting diode 100 is small in relation to the diameter of lens 70 so that it has minimal effect upon the passage of light from lens 70 to lens 76 or from lens 76 to lens 70. Light emitting diode 100 is connected to a connector 102, mounted to the outer surface of cylindrical holder 72. Connector 102 may be connected to a source of power in order to couple power to light emitting diode 100. When power is coupled to light emitting diode 100, it will illuminate and the light produced thereby will be projected out of first optical detector 56 by way of lens 70 as a beam of light. The beam size will be on the order of the diameter of lens 70 and it will be an unfocused beam of light. Light emitting diode 100 is employed for synchronizing the cell stream droplet formation and droplet charging. Its use and operation will not be further discussed in this application.

Referring again back to the photoanalysis apparatus 10, the light scattered by passage of cells in cell stream 50 through laser beam 18 at first location 40 will be coupled to the second optical detector 58. Second optical detector 58 is aligned with and opposite to mounting block carrier 32 so that laser beam 18 passes to and strikes detector 58. Detector 58 is fixedly mounted to a support block 108 which is fixedly mounted in photoanalysis apparatus 10. Detector 58 includes a cylindrical hollow housing 110 in which is mounted the various components comprising detector 58. Moving from front to rear through the housing, a rectangular elongated opaque bar 112 extends across the diameter of housing 110. Bar 112 is directly in line with laser beam 18 and acts as a field stop, blocking laser beam 18 from further entry into cylindrical housing 110. Field stop 112 occupies only a small portion of the circumference of cylindrical housing 110 so that the light scattered at first location intersection 40 can pass into cylindrical housing 110. Immediately behind field stop 112 a converging lens 114 is mounted and is held in place by retainer rings 116 and 118. Converging lens 114 in the embodiment shown is of a prescribed diameter and of a prescribed focal length. That is, any parallel beams of light received by lens 114 will be focused at a particular point in space a predetermined distance behind the lens, that distance being equivalent to one focal length.

Proceeding further into cylindrical housing 110, filter 120 may be mounted therein which filters extraneous and undesired light. Mounted behind the filter is a photodetector 122 which receives light coupled from lens 114 in the form of a light pattern and converts the light pattern into electrical signals for identifying the particular scatter pattern of the detected cell. The photodetector 122 in the embodiment consists of two large area photovoltaic cells connected in parallel.

Photodetector 122 is located at a distance of one focal length behind lens 114. By positioning the detector one focal length behind converging lens 114 advantage is taken of the inherent ability of a converging lens or lens system to perform a two dimensional optical Fourier transform.

In an optical Fourier transform, the intensity versus angle distribution of light scattered from a point is transformed into intensity versus distance from the optical axis. An important and apparently heretofore unrecognized property of the transform in flow system analysis of cells is that the intensity component is spatially invarient. That is to say, as long as the scatter produced at a particular point such as first location intersection 40 is at that particular point or within a particular area, the intensity component in the transform plane, that is at photodetector 122, remains constant notwithstanding motion of the scatter producing object. Stating this another way, a cell in cell stream 50 causes the scatter of laser beam 18. As the cell moves vertically through first location intersection 40, one would expect that the scattern pattern when referenced to any fixed point in space would change in character. Although this may be true, the scatter pattern, when transformed by means of an optical Fourier transform will produce a pattern of light intensity at photodetector 122 which does not vary even with vertical motion of the particle as it moves along through first location intersection 40 in cell stream 50. It should be noted that lenses 22 and 26 so process the laser beam 18 as to produce a region of relatively flat laser intensity at intersection 40.

It also is desirable that first location 40 be at the front focal point of the lens. However, it has been found that precisely locating location 40 at the front focal point of lens 114 is unnecessary and a substantial tolerance is acceptable without any substantial effect on the resultant light intensity pattern produced at photodetector 122. The only requirement which must be met is the positioning of photodetector 122 substantially one focal length behind lens 114 and, of course, the use of the converging lens or lens system.

By employing an optical Fourier transform system for the second optical detector 58 as above described, the scatter detection becomes substantially insensitive to the movement of the detected cell vertically through the laser beam 18 and the relative positioning of cell stream 50 with respect to second optical detector 58. Additionally, and equally as importantly, because of this positional insensitivity the use of the Fourier optical transform substantially simplifies the alignment and adjustment procedure in a photoanalysis apparatus which includes two optical detectors, one for fluorescent detection and the second for scatter detection, because precise alignment of the scatter detector 58 with respect to detector 56, cell stream 50, and laser beam 18 is no longer necessary.

In order to initialize photoanalysis apparatus 10 and prepare it for proper operation, the following alignment procedure is employed. First, lever arm 84 is moved to the solid line position shown in FIG. 3 so that light support bar 88 and light emitting diode 90 are moved into position directly behind aperture 78 in aperture plate 80. A source of power is connected to connector 94 causing illumination of light emitting diode 90. Illumination of diode 90 will result in a light image appearing at the front focal plane of lens 70. This light image will appear as a dot or circle in space a predetermined distance in front of lens 70 as previously discussed. A technician looking through the eyepiece of microscope 12 may then focus microscope 12 on the light image appearing in space so that a visual focus at the point of alignment is provided.

Next, the diluted sample and sheath flow is initialized to produce a cell stream 50 exiting from ejection nozzle 46. This cell stream is moved towards and away from first optical detector 56 by movement of mounting block carrier 32 until the stream is focused in the microscope field of view thus indicating that the stream is in the same plane as the light image previously described. Mounting block 34 is then moved in the direction indicated by arrow 36 by way of adjustment screw 38 until the cell stream 50 is positioned directly along the vertical axis of the light image formed in space. When properly aligned, a yellow disc of light will appear to be split in half vertically by the cell stream 50. At this point in time, the cell stream is aligned with first optical detector 56 and first location intersection 40 is identified by the disc of light.

Laser 16 is now energized producing laser beam 18. First lens holder 24 is moved by way of the adjustment screw thereon in order to move laser beam 18 toward or away from first optical detector 56 until beam 18 intersects cell stream 50. When beam 18 intersects cell stream 50, the second lens holder 28 is moved up and down causing laser beam 18 to move up and down through cell stream 50. Second lens holder 28 and second lens 26 are moved in this manner until laser beam 18 strikes stream 50 and intersects the center of the light image projected from first optical detector 56. Now cell stream 50, optical bench 20, laser beam 18 and first optical detector 56 are aligned with respect to one another. Lever arm can now be moved to its second position and the source of power disconnected from connector 94. Second optical detector 58 is substantially aligned with respect to laser beam 18 and cell stream 50 simply by its mounting location in apparatus 10. As previously noted, cell stream 50 will be at approximately one focal length in front of lens 114 and, this is sufficient for proper alignment of detector 58. The entire alignment procedure is now complete and photoanalysis apparatus 10 may now be utilized for detecting and analyzing cells.

While the present invention has been described by reference to a specific example and specific method, it it to be understood that modifications may be made by those skilled in the art without actually departing from the invention shown and described herein. It is therefore intended that the appended claims cover all variations that fall within the scope and spirit of this invention.

What is desired to be secured by Letters Patent of the U.S. is:

1. An apparatus for simultaneous optical measurement of several characteristics of each particle of a group of small particles while the particles are suspended in a liquid including in combination:
   a sample passage means through which the particles pass,
   a first optical detector for receiving light from said sample passage means and for developing first detection signals in response to said received light,
   means for moving one of said sample passage means and said optical detector with respect to the other for aligning one with respect to the other,
   a source of light,
   means for directing light from said light source to said sample passage means and for aligning said light and sample passage means,
   a second optical detector for receiving light from said sample passage means and for developing second detection signals in response to said received light, said second detector including a converging lens for receiving said light from said sample passage means and photodetector means positioned a predetermined distance from said focusing lens for receiving said light from said lens, said predetermined distance selected such that the light pattern received by said photodetector due to the passage of a particle through the sample passage means will maintain a substantially constant intensity with movement of any of said sample passage means, particle and light whereby said detector means is insensitive to the movement of any of said sample passage means, first optical detector, light source and particle.

2. The apparatus of claim 1 wherein said predetermined distance is selected such that a two-dimensional optical Fourier transform is performed on the light received by said second detector.

3. The apparatus of claim 1 wherein said focusing lens has a particular focal length and said photodetector means is positioned at a distance of approximately one focal length from said lens.

4. The apparatus of claim 3 wherein said photodetector is a photovoltaic diode.

5. The apparatus of claim 1 wherein said first optical detector is a fluorescence detector and said second optical detector is a scatter detector.

6. The apparatus of claim 1 wherein said means for directing light includes a lens system and carrier for said system, said lens system and carrier being movable for aligning said light and sample passage means.

7. The apparatus of claim 1 wherein said first and second optical detector are substantially fixedly secured and said means for moving moves said sample passage means for aligning same with respect to said first optical detector.

8. The apparatus of claim 7 wherein said means for directing light includes a lens system and carrier for said system, said lens system and carrier being movable for aligning said light and sample passage means.

9. The apparatus of claim 8 wherein said means for moving said sample passage means is secured to sid means for directing light.

10. The apparatus of claim 1 wherein said source of light is a laser and said light is a laser beam.

11. The apparatus of claim 1 wherein said sample passage means include a discharge device for discharging said particles in a liquid stream, an air gap through which gap said stream containing particles passes, and a receiving device for receiving said stream containing particles after passage through said air gap.

12. The apparatus of claim 9 wherein said sample passage means include a discharge device for discharging said particles in a liquid stream, an air gap through which gap said stream containing particles passes, and a receiving device for receiving said stream containing particles after passage through said air gap.

13. The apparatus of claim 12 wherein said means for moving said sample passage means include a bracket secured to said discharge device and the said receiving device for holding and moving same.

14. The apparatus of claim 1 wherein said first optical detector includes light means for developing a light, said detector including means for projecting a light image from said light means at a particular distance from the detector, said sample passage means being positioned at said light image for aligning said sample passage means with respect to said first optical detector.

15. The apparatus of claim 14 wherein said first optical detector includes a photodetector, said projection means include lens means having a particular focal length, said light image being projected to and formed at a distance of said focal length from said lens means in front of said first optical detector.

16. The apparatus of claim 15 wherein said light means include a light mounting device and a light mounted thereon, said light mounting device movable to a first position for projecting said light image and to a second storage position.

17. The apparatus of claim 15 wherein said lens means further receives light from said sample passage means and projects said received light to said photodetector.

18. The apparatus of claim 1 wherein said first optical detector includes, a housing for mounting and enclosing a photodetector, said housing including a first wall with a path formed therein for allowing light to enter and strike said photodetector, light means mounted in said housing and adapted to be moved to a first position between said wall and said detector for directing a light beam out of said housing through said path, said light means adapted to be moved to a second storage position out of said path.

19. The apparatus of claim 18 wherein said photodetector has a first light sensitive face positioned in a plane parallel to the plane of said first wall and spaced apart therefrom.

20. The apparatus of claim 19 wherein said light means include a light and light support means pivotally mounted to said housing and seating said light, said light support means adapted to be pivoted to move said light to said first position and pivoted to move said light to said second storage position.

21. The apparatus of claim 20 wherein said light support means is pivotally secured to said first wall.

22. The apparatus of claim 21 wherein said light support means include a shaft extending through said first wall and rotatably seated thereon, said shaft having a first end extending interior to said housing and a second end extending exterior to said housing, a light support arm secured to said shaft first end and mounting said light, and a lever arm secured to said second end, said lever arm being pivotable to a first position for pivoting said light and the light support arm between said photodetector and said first wall path, said lever arm being pivotable to a second position for pivoting said light and light support arm to said second storage position out of said path.

23. The apparatus of claim 19 wherein said path includes a first aspherical lens for receiving light from a source exterior to said housing and forming said received light into parallel beams of light, a second aspherical lens for receiving said parallel beams of light and focusing said beams at an image aperture positioned a predetermined distance from said second lens and between said second lens and said photodetector, said image aperture passing said focused beams to said photodetector.

24. The apparatus of claim 23 wherein said light means include a light positioned between said image aperture and said photodetector, said light movable to a first position for passing light through said image aperture and to a second storage position.

25. An apparatus for the simultaneous optical measurement of several characteristics of a group of small particles while the particles are suspended in a liquid including in combination,
sample passage means for moving said liquid containing particles in a stream through a first point.
a source of light for developing a light beam,
beam directing means for directing said light beam to said first point for producing resultant light thereat in accordance with particle characteristics in said stream,
first optical detector means for receiving said resultant light and for developing first detection signals in response thereto, said sample passage means, beam directing means and first optical detector means being movable with respect to one another for properly aligning said first detector means, beam, sample passage means and first point with respect to one another, and
second optical detector means including a focusing lens for receiving said resultant light and for coupling said light at a predetermined distance from said lens and photodetector means positioned at said predetermined distance from said lens and operative to develop second detection signals in response to said light from said lens, said predetermined distance being selected such that the light received by said photodetector means will form a pattern thereat having substantially constant intensity with movement of any of said sample passage means, particles, beam, beam directing means and first optical detector means whereby said photodetector means is insensitive to movement of said sample passage means, particles, light source and first optical detector.

26. The apparatus of claim 25 wherein said focusing lens has a particular focal length and said photodetector means is positioned at a distance of approximately one focal length from said lens.

27. The apparatus of claim 26 wherein said focusing lens is a converging lens.

28. The apparatus of claim 27 wherein said photodetector is a photovoltaic diode.

29. A method for adjusting an apparatus for simultaneous measurement of several characteristics of each particle of a group of small particles suspended in a liquid wherein the apparatus includes a light source that develops a light beam, beam directing means, sample passage means for moving said liquid in a stream through a first location, a first optical detector and a second optical detector including a converging lens and photodetector, said method including the steps of:
moving said first optical detector and the sample passage means relative to one another for aligning said first optical detector and said first location,
moving said beam directing means and sample passage means relative to one another for directing said light beam from said source to said first location while maintaining alignment of said first optical detector and first location,
aligning said converging lens with said first location and
positioning said photodetector a predetermined distance from said converging lens for receiving light therefrom,
selecting said predetermined distance such that the light received at said photodetector will form a pattern having substantially constant intensity with movement of any of said sample passage means, particle and light beam so that the photodetector is insensitive to movement of said sample passage means, particles, light beam, beam directing means and first detector.

30. The method of claim 29 wherein the step of selecting said predetermined distance includes the step of selecting said distance such that an optical Fourier transform is performed on the light received by said lens and coupled to said photodetector.

31. The method of claim 29 wherein said focusing lens has a particular focal length and wherein the step of positioning said photodetector includes the step of positioning said photodetector at a distance of approximately one focal length of said lens from said lens.

32. The method of claim 29 wherein the step of aligning said first detector and sample passage means include the steps of:
projecting a light image from said first detector to a location a predetermined distance from said first optical detector and positioning the liquid stream formed by said sample passage means at said location such that said light image appears in said stream and at said first location.

33. A housing for mounting and enclosing a photodetector, said housing including a first wall with a path formed therein for allowing light to enter and strike said photodetector, light means mounted in said housing and adapted to be moved to a first position between said wall and said detector for directing a light beam out of said housing through said path, said light means adapted to be moved to a second storage position out of said path.

34. The housing of claim 33 wherein said photodetector has a first light sensitive face positioned in a plane parallel to the plane of said first wall and spaced apart therefrom.

35. The housing of claim 34 wherein said light means include a light and light support means pivotally mounted to said housing and seating said light, said light support means adapted to be pivoted to move said light to said first position and to move said light to said second storage position.

36. The housing of claim 35 wherein said light support means is pivotally secured to said first wall.

37. The housing of claim 36 wherein said light support means include a light support arm positioned interior to said housing, a shaft secured to said light support arm and passing through said first wall, and a lever arm secured to said shaft and extending exterior to said housing.

38. The housing of claim 36 wherein said light support means include a shaft extending through said first wall and rotatably seated therein, said shaft having a first end extending interior to said housing and a second end extending exterior to said housing, a light support arm secured to said shaft first end and mounting said light and a lever arm secured to said second end, said lever arm being pivotable to a first position for pivoting said light and light support arm between said photodetector and said first wall path, said lever arm being pivotable to a second position for pivoting said light and light support arm to said second storage position out of said path.

39. The housing of claim 38 further including detent means for holding said lever arm in one of said first and second positions.

40. The housing of claim 38 wherein said light support means shaft is hollow, said light support means further including conductor means coupled to said light and passing through said shaft for coupling power to said light.

41. The housing of claim 40 wherein said support means further include electrical connector means secured to said lever arm and connected to said conductor means, said connector means adapted to be connected to a source of power for coupling power to said light.

42. The housing of claim 33 wherein said path formed in said wall includes first and second lenses and an image aperture arranged and spaced apart for focusing light from an object a predetermined distance exterior to said first wall into said aperture.

43. The housing of claim 33 wherein said path includes a first aspherical lens for receiving light from a source exterior to said housing and forming said received light into parallel beams of light, a second aspherical lens for receiving said parallel beams of light and focusing said beams at an image aperture positioned a predetermined distance from said second lens and between said second lens and said photodetector, said image aperture passing said focused beams to said photodetector.

44. The housing of claim 43 wherein said light means includes a light and light support arm pivotably mounted to said housing and positioned between said image aperture and said photodetector, said light movable to said first position for passing light through said image aperture and to a second storage position.

45. The housing of claim 43 wherein said path further includes, second light means positioned in said path between said first and second lens, said second light means operative to direct a second light beam through said first lens and out of said housing.

46. The housing of claim 45 wherein said second light means and said second light beam is small relative to the first lens diameter.

47. The housing of claim 33 wherein said photodetector is a photomultiplier tube having a generally cylindrical form with an end wall forming a photosensitive screen, said housing being cylindrical and enclosing said photomultiplier tube, said housing first wall being a housing end wall positioned adjacent to and in a plane parallel to said photosensitive screen.

48. The housing of claim 47 wherein said light means include, a shaft extending through said housing end wall and rotatably seated therein, said shaft having a first end extending interior to said housing and second end extending exterior to said housing, a light support arm having a first end secured to said shaft first end and a light mounted on a second end, a lever arm secured to said shaft second end, said lever arm being pivotable to a first position for pivoting said light and light support arm between the center of said photomultiplier tube photosensitive screen and said housing end wall into said path, and being pivotable to a second position for pivoting said light and light support arm to said second storage position out of said path.

49. The housing of claim 48 wherein said light is a light emitting diode.

50. The housing of claim 49 wherein said shaft is hollow, said light means further including conductor means coupled to said light and passing through said shaft and electrical connector means secured to said lever arm and connected to said conductor means, said connector means adapted to be connected to a source of power for coupling power to said light.

51. In a system wherein a source of light is passed through an object and light from the object is coupled to a light sensitive detector mounted in a light shielding housing behind an apertured image plane which aperture is aligned with the detector center, and wherein the detector center must be aligned with the object, the improvement comprising, means for visually aligning said detector center, and object including a second light source secured to said housing between said apertured image plane and said detector and adapted to be moved into alignment with the detector center and image plane aperture for directing a light beam through said image plane aperture to said object position for alignment thereof.

52. The system of claim 51 wherein said means for visually aligning include, a shaft extending through said housing and rotatably seated therein, said shaft having a first end extending interior to said housing and a second end extending exterior to said housing, a light support arm having a first end secured to said shaft first end and said second light source mounted on a second end, a lever arm secured to said shaft second end, said lever arm being pivotable to a first position for pivoting said second light source and light support arm between the center of the detector and the aperture in the apertured image plane and pivotable to a second position for pivoting said second light source and light support arm to said second storage position out of alignment with the detector center and said aperture in the image plane.

53. The system of claim 52 wherein said second light source is a light emitting diode.

54. The system of claim 53 wherein said shaft is hollow, said means for visually aligning further including conductor means coupled to said second light source and passing through said shaft and electrical connector means secured to said lever arm and connected to said conductor means, said connector means adapted to be connected to a source of power for coupling power to said light.

* * * * *